US011911320B2

(12) United States Patent
Brody

(10) Patent No.: US 11,911,320 B2
(45) Date of Patent: *Feb. 27, 2024

(54) SURGEON SUPPORT SYSTEM FOR OPERATING TABLES

(71) Applicant: RC Medical LLC, Cottonwood Heights, UT (US)

(72) Inventor: Fredrick Brody, Bethesda, MD (US)

(73) Assignee: RC MEDICAL LLC, Cottonwood Heights, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/157,583

(22) Filed: Jan. 20, 2023

(65) Prior Publication Data

US 2023/0157919 A1 May 25, 2023

Related U.S. Application Data

(63) Continuation of application No. 17/560,800, filed on Dec. 23, 2021, now abandoned, which is a continuation of application No. 16/392,288, filed on Apr. 23, 2019, now Pat. No. 11,213,449.

(51) Int. Cl.
*A61G 13/12* (2006.01)
*A61G 13/10* (2006.01)

(52) U.S. Cl.
CPC ........... *A61G 13/12* (2013.01); *A61G 13/101* (2013.01)

(58) Field of Classification Search
CPC .... A61G 13/101; A61G 13/12; A61G 7/0507; A61G 7/052; A61G 7/0521; A61G 7/0522; A61B 90/60; A47C 19/02; A47C 21/08

See application file for complete search history.

(56) References Cited

U.S. PATENT DOCUMENTS

| 421,656 | A | * | 2/1890 | Blanken | A61G 7/0507 5/425 |
| 4,089,497 | A | * | 5/1978 | Miller | A47B 95/043 5/663 |
| 4,109,887 | A | * | 8/1978 | Wakeland, Jr. | A47C 27/085 5/663 |
| 4,214,326 | A | * | 7/1980 | Spann | A47C 20/027 5/632 |
| 4,215,446 | A | | 8/1980 | Mahoney | |
| 4,672,698 | A | * | 6/1987 | Sands | A61G 7/0522 5/663 |
| 4,916,767 | A | * | 4/1990 | Uetake | A47C 27/081 5/663 |

(Continued)

FOREIGN PATENT DOCUMENTS

EP 3315107 A1 5/2018
WO WO 2004/112676 A1 12/2004

*Primary Examiner* — Justin C Mikowski
*Assistant Examiner* — George Sun
(74) *Attorney, Agent, or Firm* — Thorpe North & Western; Jason R. Jones

(57) ABSTRACT

Systems and methods of providing an attendant support on an operating table include obtaining a cushion presenting an attendant support surface and coupling the cushion to a rail of the operating table such that the attendant support surface of the cushion is oriented at least partially laterally outward from the rail. The attendant support surface is operable to provide support to an attendant positioned adjacent to and leaning against the operating table.

20 Claims, 8 Drawing Sheets

(56) References Cited

U.S. PATENT DOCUMENTS

| | | | |
|---|---|---|---|
| 4,966,351 A * | 10/1990 | Klepacki | A61G 13/0009 |
| | | | 5/649 |
| 5,163,197 A * | 11/1992 | Armstrong | A47C 27/085 |
| | | | 5/663 |
| 5,423,093 A * | 6/1995 | Hall-Vandis | E04H 4/14 |
| | | | 5/663 |
| 5,450,641 A | 9/1995 | Montgomery | |
| 5,867,853 A * | 2/1999 | Feld | A47C 19/021 |
| | | | 5/663 |
| 5,890,244 A * | 4/1999 | Cartwright | A61G 7/0522 |
| | | | 5/663 |
| 5,926,876 A * | 7/1999 | Haigh | A61G 13/12 |
| | | | 5/616 |
| 6,076,212 A * | 6/2000 | Feld | A47C 19/021 |
| | | | 5/663 |
| 6,298,507 B1 | 10/2001 | Clyburn | |
| 6,401,281 B1 * | 6/2002 | Younge | A47C 21/08 |
| | | | 5/663 |
| 6,622,323 B2 * | 9/2003 | Zerhusen | A61G 7/0509 |
| | | | 5/663 |
| 8,268,432 B2 | 9/2012 | Malcolm | |
| 8,286,283 B2 | 10/2012 | Copeland et al. | |
| 9,125,500 B2 | 9/2015 | Farrell | |
| 2003/0204909 A1 | 11/2003 | Lane | |
| 2004/0133984 A1 * | 7/2004 | Mahoney | A61G 13/0072 |
| | | | 5/651 |
| 2005/0081295 A1 * | 4/2005 | Malcolm | A61G 13/125 |
| | | | 5/624 |
| 2006/0242765 A1 * | 11/2006 | Skripps | A61G 13/04 |
| | | | 5/624 |
| 2014/0007408 A1 * | 1/2014 | Nool | B65D 25/22 |
| | | | 29/525.01 |
| 2015/0052684 A1 * | 2/2015 | Farrell | A61G 7/0522 |
| | | | 5/663 |
| 2015/0250672 A1 * | 9/2015 | Fossez | A61G 13/125 |
| | | | 5/630 |
| 2019/0262204 A1 * | 8/2019 | Hertz | A61G 13/04 |
| 2020/0022860 A1 * | 1/2020 | Van Doorn | A61G 13/101 |

* cited by examiner

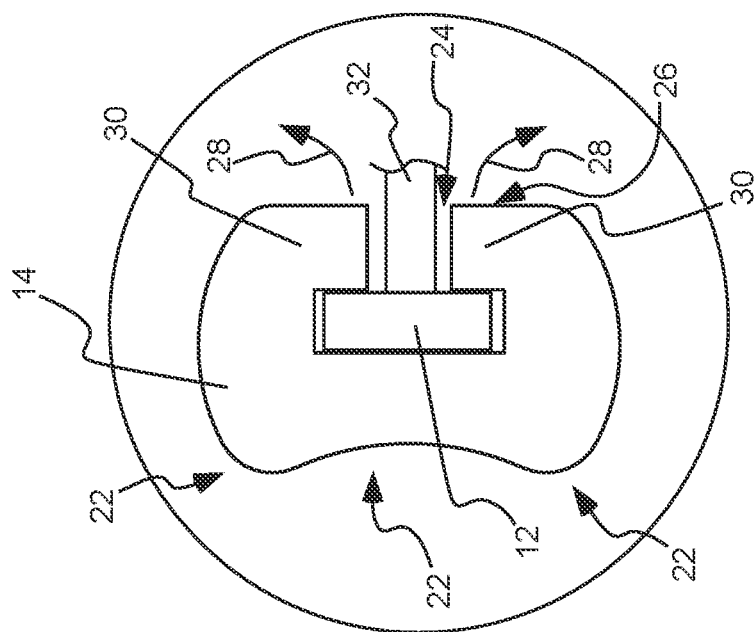
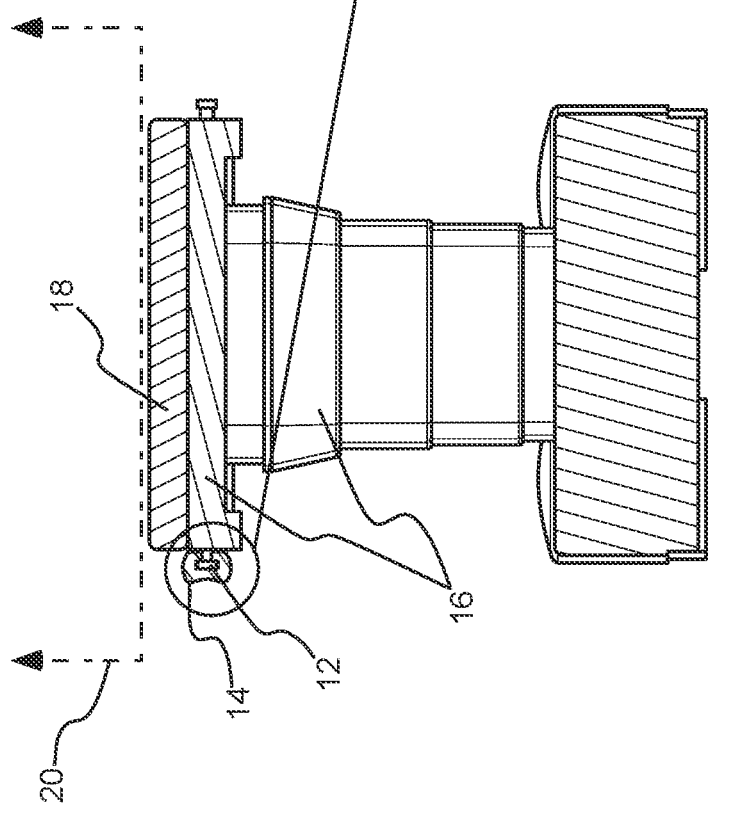
FIG. 3C
FIG. 3B

SURGEON SUPPORT SYSTEM FOR OPERATING TABLES

PRIORITY CLAIM

This is a continuation of U.S. patent application Ser. No. 17/560,800, filed Dec. 23, 2021, which is a continuation of U.S. patent application Ser. No. 16/392,288, filed Apr. 23, 2019, and issued Jan. 4, 2022 as U.S. Pat. No. 11,213,449, each of which is hereby incorporated herein by reference in its entirety.

BACKGROUND OF THE INVENTION

Field of the Invention

The present technology relates generally to systems and methods employed in operating rooms to alleviate physical discomfort experienced by surgical attendants during and after surgical procedures.

Related Art

Surgical tables, or "operating tables," as that term is used herein, are used during surgery to provide a stable and sterile surface on which a patient's body can be supported during surgery. As surgical procedures can often last for many hours, operating tables generally include a cushioned pad or surface upon which the patient is laid. This padding reduces post-operative sores and irritation that might otherwise be experienced by the patient at various pressure points between the patient and the operating table.

While various strategies exist to minimize patient irritation during surgery, few strategies exist to alleviate surgeon discomfort during extended operative cases. Surgeons must maintain a standing position for many hours during such procedures, oftentimes leaning against the lateral edges of the operating table for support. Surgeons and supporting staff can perform multiple operations during any given shift. They often continue leaning against the lateral rail or edge of the operating table for many hours.

SUMMARY OF THE INVENTION

In accordance with one aspect of the technology, an operating table assembly is provided, including a base and a patient support surface carried by the base. The patient support surface can be configured to receive and support a patient thereon. A rail can be carried by the base. The rail can extend along a lateral side of the operating table, the rail being disposed vertically lower than the patient support surface and presenting an inner surface, proximal to the base and an outer surface, distal from the base. A cushion can be coupled to the rail, the cushion having an inner surface proximal to and contacting the outer surface of the rail and an outer surface located distally from the outer surface of the rail, the outer surface of the cushion presenting an attendant support surface disposed vertically lower than the patient support surface and oriented at least partially laterally outward from the rail, the attendant support surface operable to provide support to an attendant positioned adjacent to and leaning against the operating table.

In accordance with another aspect of the technology, a method is provided of providing an attendant support on an operating table. The method can include obtaining a cushion having an inner surface and an outer surface, the outer surface presenting an attendant support surface. The cushion can be coupled to the rail of the operating table such that an inner surface of the cushion is proximal to and contacts an outer surface of the rail and the attendant support surface of the cushion is disposed vertically lower than the patient support surface and distal to the outer surface of the rail and is oriented at least partially laterally outward from the rail, the attendant support surface being operable to provide support to an attendant positioned adjacent to and leaning against the operating table.

In accordance with another aspect of the invention, a kit is provided, including a cushion, coupleable to a rail of an operating table. The cushion can present an attendant support surface orientable at least partially laterally outward from the rail when the cushion is coupled to the rail, the attendant support surface being disposed vertically lower than the patient support surface and being operable to provide support to an attendant positioned adjacent to and leaning against the operating table. The cushion can include a rail opening on a side of the cushion opposite the attendant support surface, the rail opening of the cushion being openable to receive at least a portion of the rail within the cushion. Instructions can be provided for attaching the cushion to the rail such that the attendant support surface is oriented laterally away from the operating table to allow the attendant to lean against the operating table when positioned laterally adjacent to the operating table.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 3B is a sectioned view of the operating table of FIG. 3A, taken along section 3B-3B of FIG. 3A;

FIG. 3C is an enlarged view of a rail and cushion of FIG. 3B;

DETAILED DESCRIPTION

Figure 1:
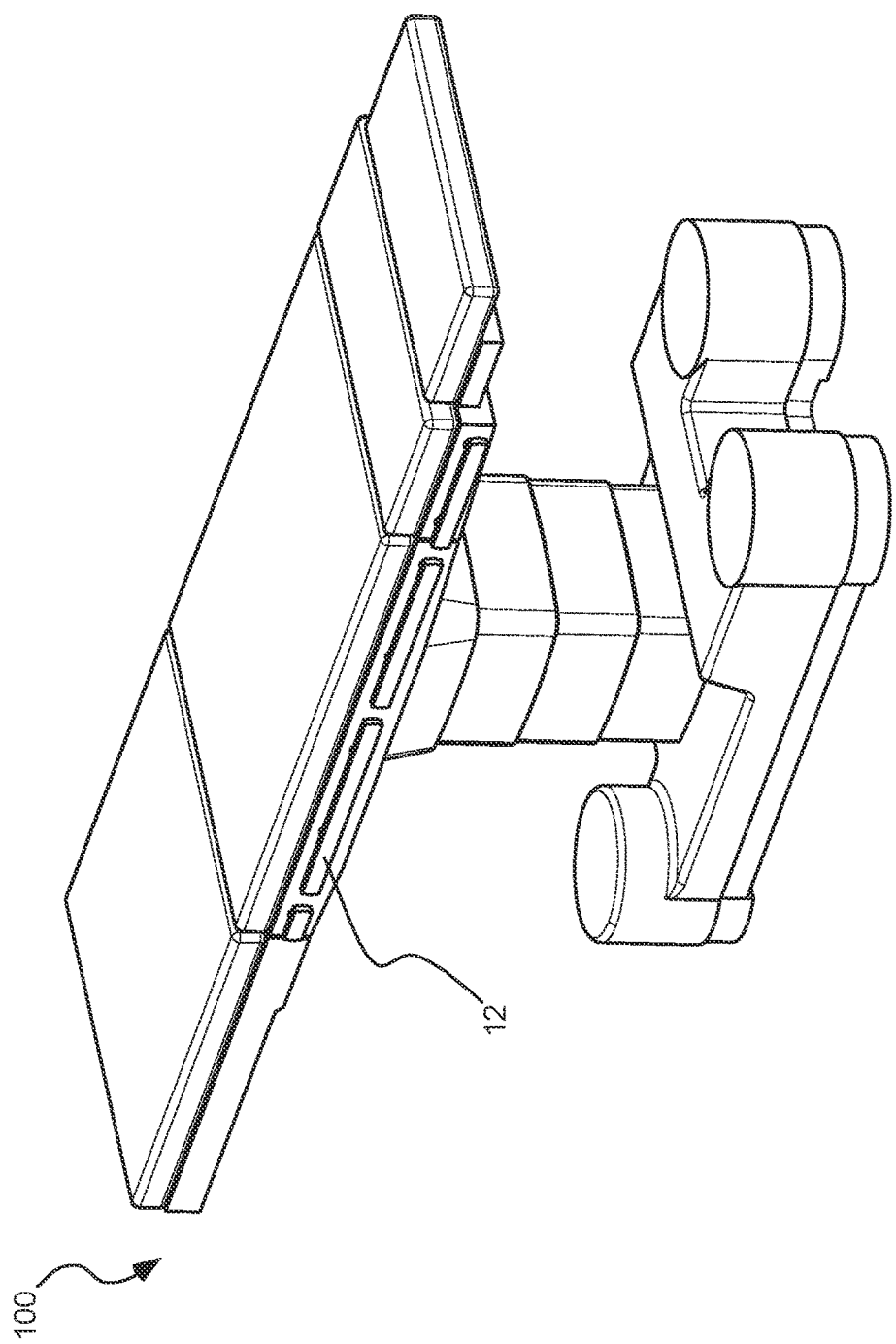
FIG. 1 is a perspective view of a Prior Art operating table.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to "a cushion" can include one or more of such cushions, if the context so dictates.

The terms "attendant" or "surgical attendant" are used herein to refer to any personnel involved in a surgical procedure. When used herein, these terms are not intended to be limited by any conventional usage of these terms. These terms are intended to encompass any of a surgeon, a technician, a nurse, an orderly, etc.

As used herein, the term "substantially" refers to the complete or nearly complete extent or degree of an action, characteristic, property, state, structure, item, or result. As an arbitrary example, an object that is "substantially" enclosed is an article that is either completely enclosed or nearly completely enclosed. The exact allowable degree of deviation from absolute completeness may in some cases depend upon the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item so long as there is no measurable effect as a result thereof.

As used herein, the term "about" is used to provide flexibility to a numerical range endpoint by providing that a given value may be "a little above" or "a little below" the endpoint.

Relative directional terms can sometimes be used herein to describe and claim various components of the present invention. Such terms include, without limitation, "distal," "proximal," "upward," "downward," "horizontal," "vertical," etc. These terms are generally not intended to be limiting, but are used to most clearly describe and claim the various features of the invention. Where such terms must carry some limitation, they are intended to be limited to usage commonly known and understood by those of ordinary skill in the art in the context of this disclosure. In some instances, dimensional information is included in the figures. This information is intended to be exemplary only, and not limiting. In some cases, the drawings are not to scale and such dimensional information may not be accurately translated throughout the figures.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

INVENTION

The present technology relates generally to systems and methods that minimize discomfort or injury experienced by medical personnel while performing surgical procedures. During a typical surgical procedure, a surgeon and/or surgical technician (referred to herein collectively as "surgical attendants") must oftentimes maintain an erect posture while performing procedures on a patient positioned upon an operating table.

Figure 3A:
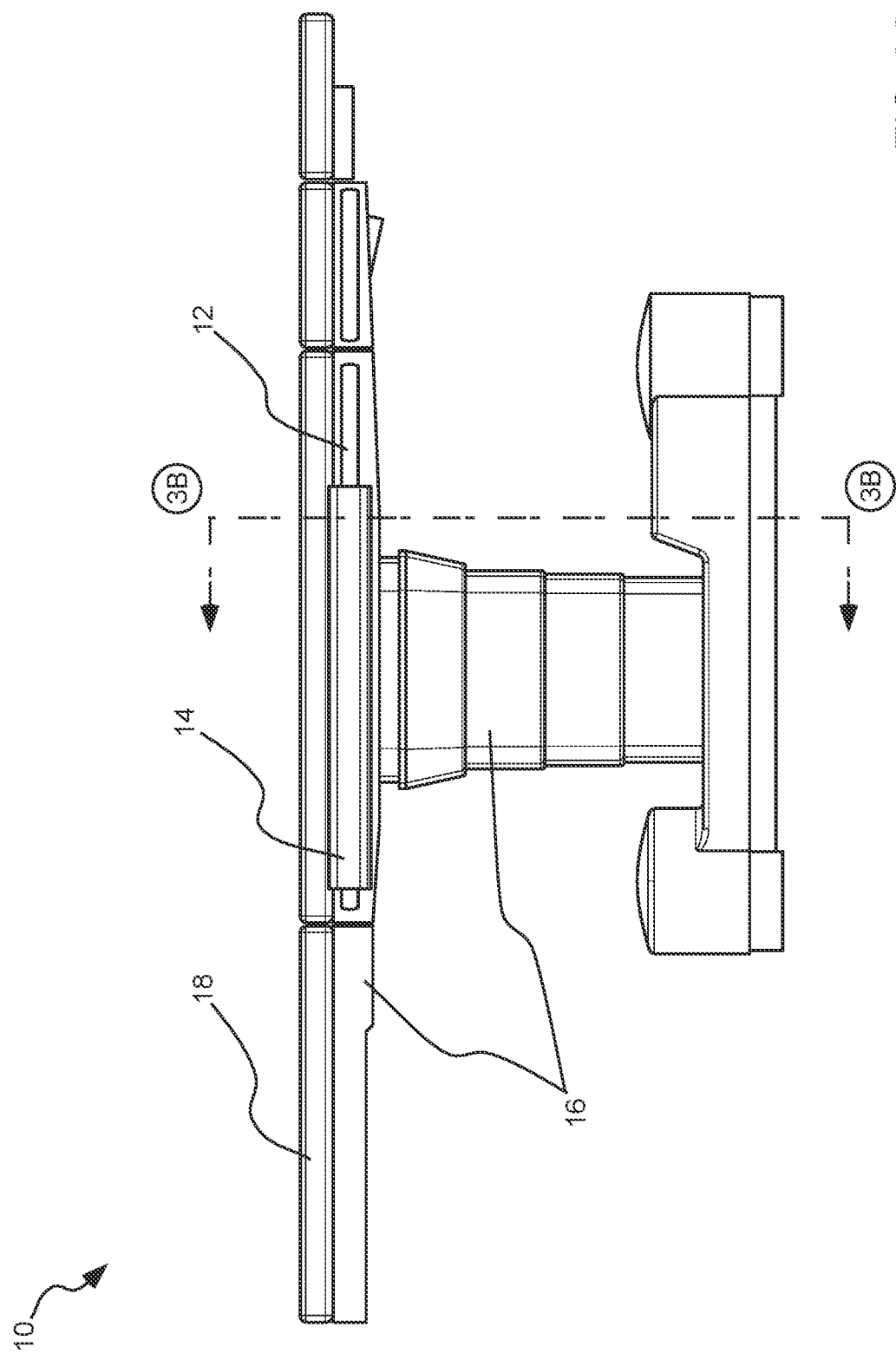
FIG. 3A is a side view of the operating table of FIG. 2.

A conventional operating table is shown at 100 in FIG. 1. Such conventional operating tables often include a rail 12 extending along a side of the table to facilitate attachment of auxiliary equipment to the operating table, such as equipment racks, trays, etc. (not shown in detail). Any such equipment generally includes an extension component that elevates the rack, tray, etc., above the rail and into the so-called sterile field so as to be accessible by the surgical team during the procedure. The sterile field is generally defined by the upper surface of the patient support surface and can extend upwardly from this plane and horizontally outward about 18 inches from the patient support surface (see 20 in FIG. 3B, for example). Any items within the sterile field must be sterile. Items beyond the sterile field (including below it) must be at least disinfected to a high level (referred to as "high level disinfection," or "HLD"). The rail, and components attached to and in the immediate vicinity of the rail, need only be maintained at HLD. Any component extending from the rail and into the sterile field, however, must be sterilized.

As the surgical attendants must often maintain an erect posture while performing tasks during surgery, they often lean against the operating table to support their weight while standing beside the table. The point of contact between the attendant's body and the operating table is often the rail 12, with the attendant's thigh resting against the rail. If this contact is maintained for any significant period of time, the attendant can experience discomfort or injury at this pressure point. Minimizing any such discomfort or injury is not only in the best interest of the surgical attendants, doing so can increase the efficacy and longevity of the attendants and can increase the likelihood of a successful surgery.

Figure 2:
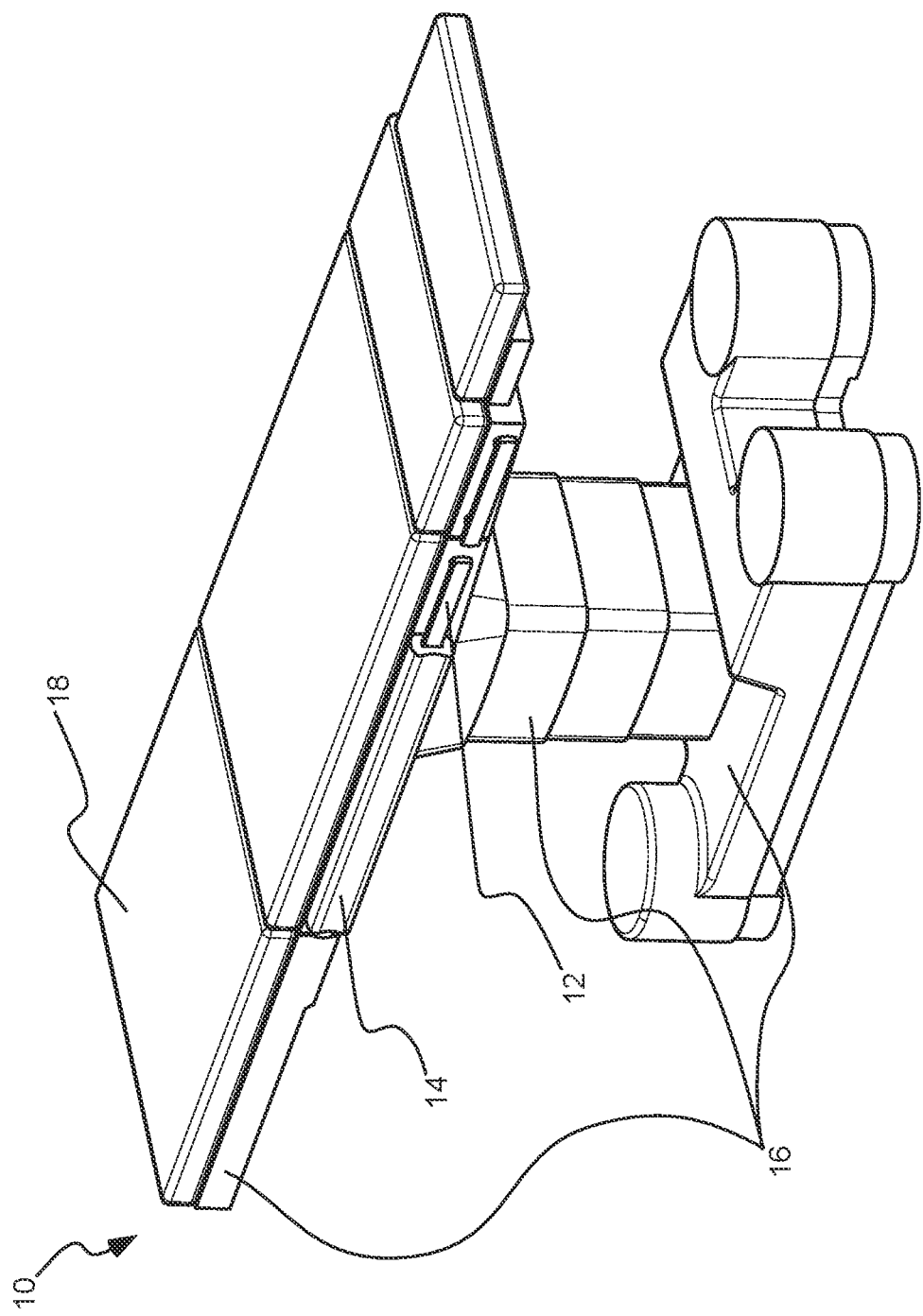
FIG. 2 is a perspective view of an operating table having an attendant cushion support coupled thereto in accordance with an aspect of the present technology.

The present technology addresses this issue by providing a cushioned interface against which surgical attendants can support their bodies during a surgical procedure. As shown in FIG. 2, in one aspect of the technology, an operating table assembly 10 is provided that can include a base 16. The base can include several components that can vary by manufacturer, table type, surgery type, etc. The base carries a patient support surface 18 that is configured to receive and support a patient thereon. Generally, the patient support surface is padded to provide a comfortable interface between the patient and the operating table. A patient support surface is generally placed atop the operating table and defines a lower vertical boundary of the sterile field (shown by example at 20 in FIG. 3B).

A rail 12 is also carried by the base 16. The rail can extend along a lateral side of the operating table and serves as a location of attachment for various auxiliary components such as trays, racks, etc. (not shown).

In the example shown, a cushion 14 is coupled to the rail. The cushion presents an attendant support surface indicated generally at 22 in FIG. 3C. The attendant support surface is oriented at least partially laterally outward from the rail so as to provide support to an attendant positioned adjacent to and leaning against the operating table. In most applications, the attendant can position his or her thigh or hip against the attendant support surface to aid in supporting the attendant during the procedure.

The cushion 14 and/or the attendant support surface 22 can be formed from a pliable and/or elastic material that compresses slightly beneath the weight of the attendant to alleviate pressure applied to the attendant's body. While the structure from which the cushion can be formed can vary, in one aspect the cushion is formed from a polymeric foam material such as polyethylene. The cushion can be extruded, molded, machined or fabricated in a number of manners to exhibit a desired size, shape, cross-section and stress/strain response. These materials have been found to provide a comfortable interface for the attendants while also being capable of high level disinfection.

In the examples shown, the cushion is a unitary structure formed from a single material, e.g., a polyethylene foam. This can simplify construction and reduce costs. In other aspects, however, the cushion can include a supporting framework or understructure (not shown in detail) to provide rigidity to the cushion assembly that can aid in attaching the attendant support surface 22 or providing structural support to the attendant support surface. Such a framework can be formed from a rigid material, such as metals or hard polymers. In addition, the cushion can be formed from one or more layers of material that vary in hardness, rigidity, porosity, etc. For example, an outer layer of the cushion may be formed from a softer, more pliable polymer, while an underlayer may be formed from a denser, more rigid polymer.

Advantageously, the cushion 14 can be coupled directly to the rail 12. In this manner, an interface between the cushion and the rail can be devoid of any additional support structure. In other words, the cushion need not (and in some cases, should not) extend long distances from the rail. This can avoid the necessity of sterilizing any portion of the cushion. In this manner, all components of both the rail and the cushion are vertically removed from the sterile field 20.

The cushion 14 can be attached to the rail 12 in a number of manners. In the examples shown, however, the cushion is removably attachable to the rail. In this manner, the cushion can quickly and easily be installed upon or removed from the rail by surgical staff. The cushion can be at least partially deformable so as to provide a form fit over the rail. This can aid in quickly installing or removing the cushion and can also simplify manufacture of the cushion. In the example shown in FIGS. 3A, 3B and 3C, the cushion 14 includes a rail opening 24 on a side 26 of the cushion opposite the attendant support surface 22. This rail opening can be openable to receive at least a portion of the rail within the cushion.

The rail opening 24 can enable the cushion 14 to be easily "snap fit" over the rail 12 in a variety of locations along the rail. As shown by directional indicators 28, two side walls 30 of the cushion can be flexed outwardly to increase the size of the rail opening 24 to allow the rail to be received in the cushion. The rail opening can also provide a location in which the cushion can extend around an anchoring leg 32 of the rail. The anchoring leg generally extends from the base of the operating table to support the rail and maintain it in a position extended from the base. By positioning the anchoring leg within the rail opening, the cushion 14 can not only be quickly and easily attached to and removed from the rail 12, it can be slidably positionable along the rail. In this manner, the cushion can be positioned in a location best for supporting the surgical attendants while also avoiding any locations necessary on the rail to support desired auxiliary structure such as racks, shelves, etc.

In addition to the rail opening shown, the rail opening can include a single sidewall 30 (not shown in detail) that can be installed behind the rail 12. In this embodiment, the side wall can be simply slid behind the rail 12 to hang the cushion from the rail.

Figures 4, 5:
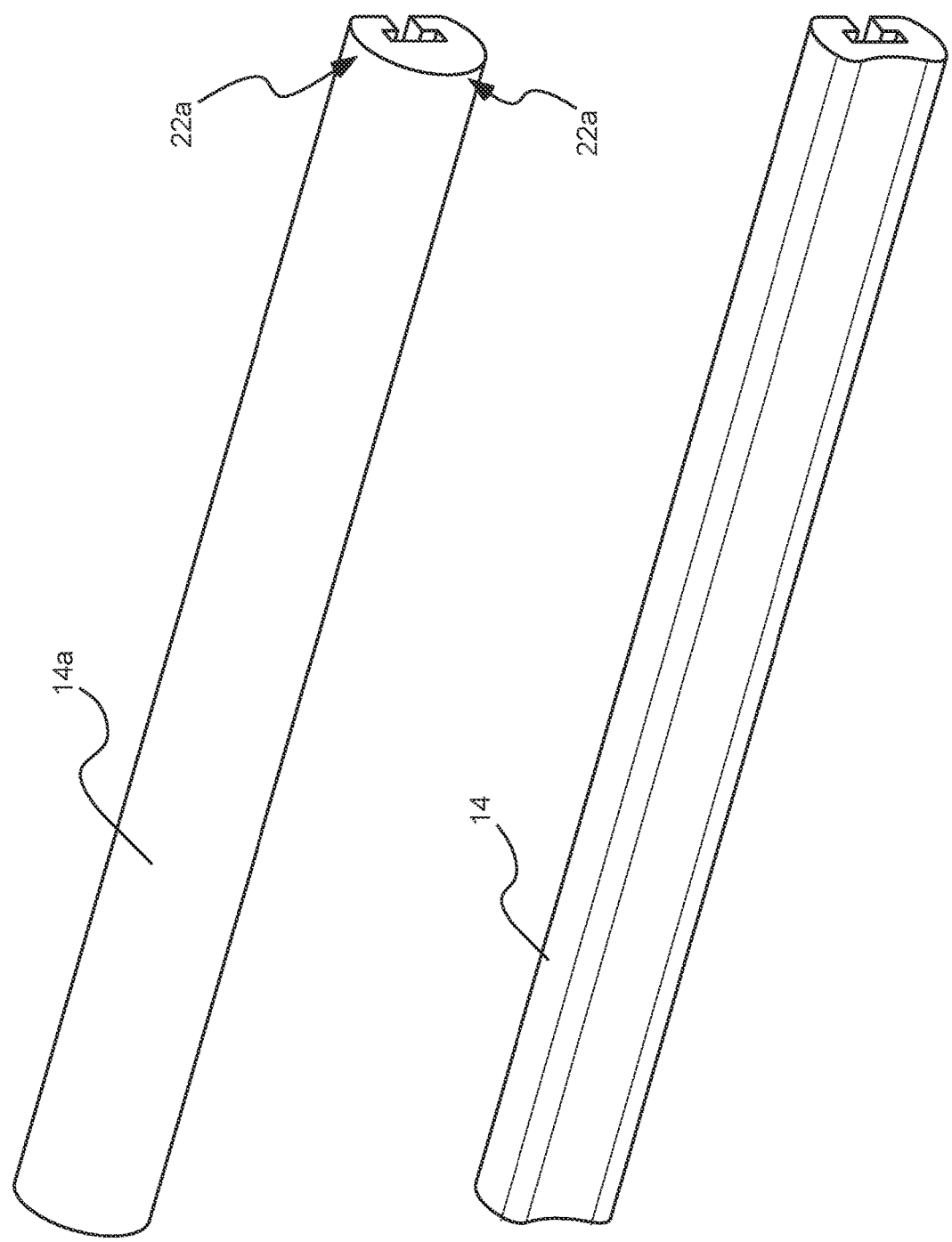
FIG. 4 is a perspective view of a cushion presenting an attendant support surface in accordance with an aspect of the technology.
FIG. 5 is a perspective view of another cushion presenting an attendant support surface in accordance with another aspect of the technology.
Figure 6:
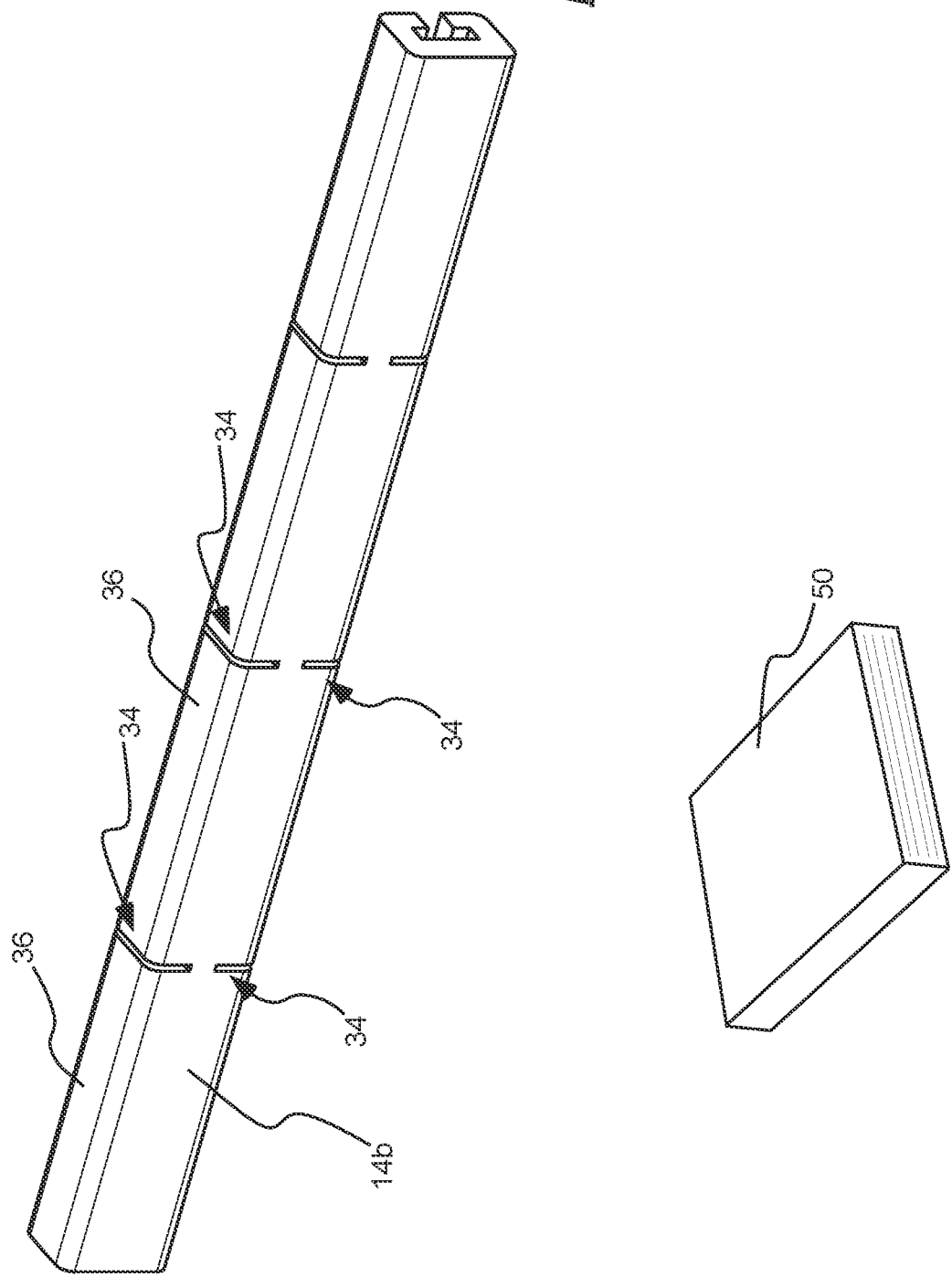
FIG. 6 includes a perspective view of a kit for attaching a cushion presenting an attendant support surface in accordance with an aspect of the technology.

FIGS. 4 through 6 illustrate various alternate configurations of cushions 14, 14a and 14b in accordance with the present technology. As shown in FIG. 4, in one example the cushion can present an at least partially arcuate attendant support surface 22a. This can increase the surface of the support surface upon which an attendant can comfortably support him- or herself.

In the example shown in FIG. 6, the cushion 14b can include one or more weakened zones 34 that define cushion segments 36. The cushion segments can be separable from one another at the weakened zones. In this manner, the cushion can be configured in the manner best for any particular surgeon, operating table and procedure. In the event only a small area is desired for supporting an attendant, a single cushion segment 36 can be created and positioned where desired. In some applications, it may be desired to separate the cushion to avoid an obstruction on or near the rail: in such case, a segment can be positioned on either side of the obstruction.

The dimensions of the cushion can vary depending upon a number of factors. In many cases, the dimensions of the rail 12 are standardized at about 1⅛ inches in height and about ⅜ in depth. The inner surface of the cushion can be sized accordingly to provide a snap-fit over the rail. The cushion walls can include a thickness of about ½ inch to about 1 inch, extending outwardly from the inner surface of the cushion.

FIG. 6 also illustrates a further embodiment in which the technology provides a kit that can include a cushion, 14b in this example, that can be couplable to a rail of an operating table. The cushion can present an attendant support surface orientable at least partially laterally outward from the rail when the cushion is coupled to the rail, the attendant support surface operable to provide support to an attendant positioned adjacent to and leaning against the operating table. The kit can include instructions 50 for attaching the cushion to the rail. The instructions can take a variety of forms and, while shown in a printed state in FIG. 6, can be provided in a variety of manners to the end user. For example, the instructions can include indicia applied to or carried by the cushion itself. The instructions can also be provided electronically, through a web portal or other digital delivery system.

Figure 7:
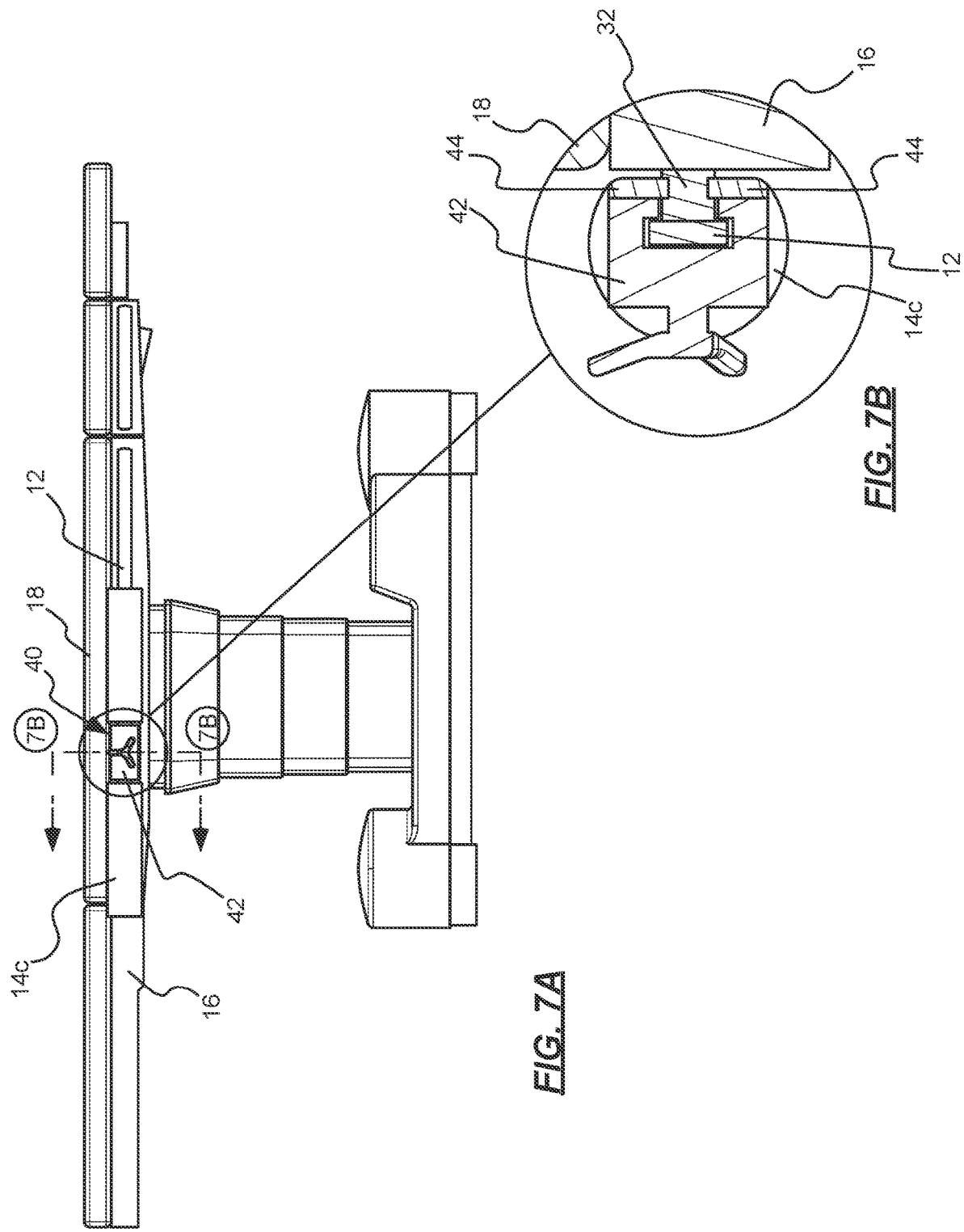
FIG. 7A is a side view of an operating table in accordance with another aspect of the present technology.
FIG. 7B is an enlarged view of a section of the operating table of FIG. 7A, taken along section 7B-7B of FIG. 7A.

FIGS. 7A and 7B illustrate another embodiment of the technology in which cushion 14c can include an access opening 40 formed therein. The access opening can allow an auxiliary device, such as clamp 42, to be attached to the rail 12 around and/or through the cushion while the cushion remains coupled to the rail. The access opening can be formed in a variety of manners that allow a clamp or other structure to be attached to the rail. In the example shown in FIG. 7B, the cushion includes one or more connectors 44 that connect opposing pieces of the cushion to one another behind or beneath the clamp. In this manner, the clamp or other auxiliary structure can be attached to the rail without requiring that sections of the cushion be removed or repositioned.

Figure 8:
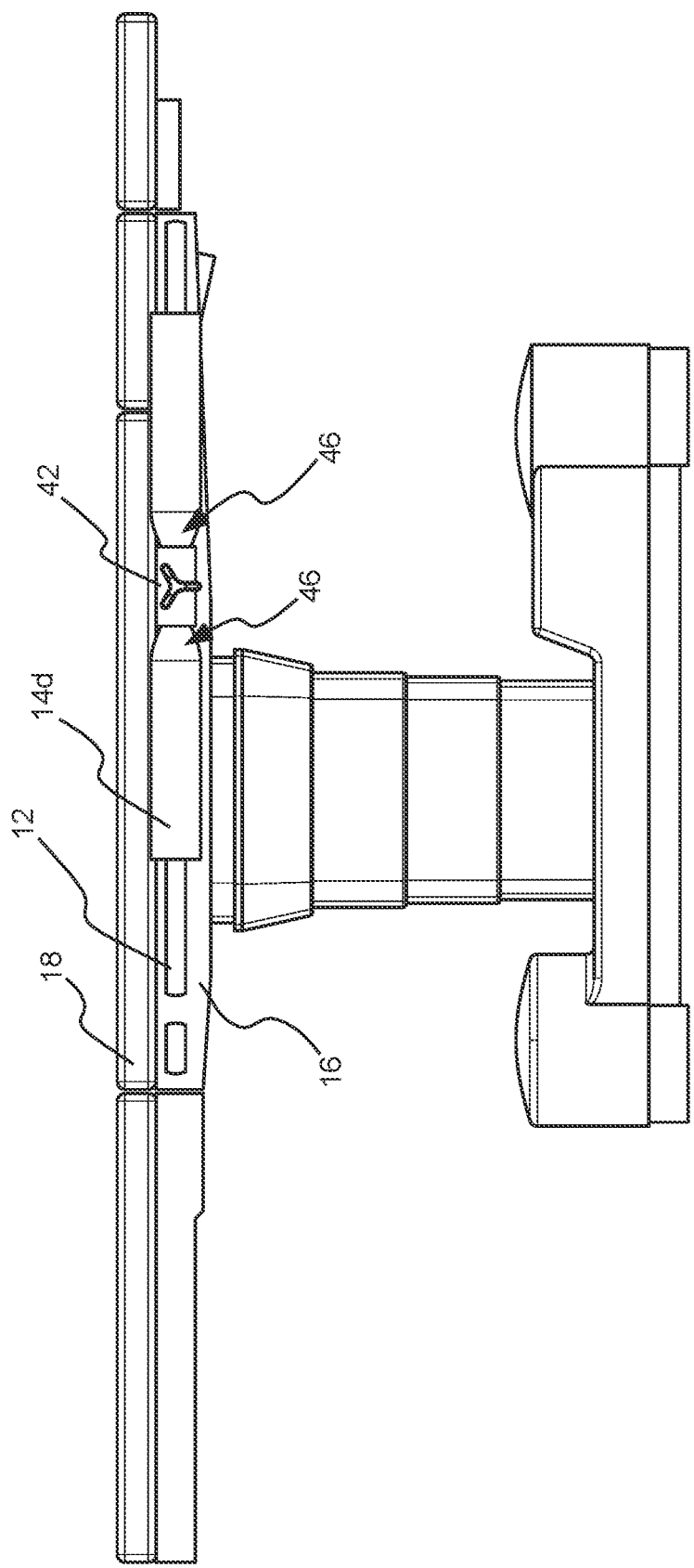
FIG. 8 is a side view of an operating table in accordance with another aspect of the present technology.

FIG. 8 illustrates a similar mechanism by which auxiliary structure or clamp 42 can be attached to rail 12 over cushion 14d. In this aspect, cushion 14d is formed from a pliable material that can be relatively easily compressed beneath the clamp 42. In practice, as the clamp is positioned over the cushion, compression zones or areas 46 are created as the cushion compresses beneath the clamp. The clamp can be attached or clamped to the rail in the usual manner: the cushion is compressed to a condition in which very little thickness interferes with normal operation of the clamp.

In addition to the structural components discussed above, the present technology also provides a method of providing an attendant support on an operating table. The method can include: obtaining a cushion presenting an attendant support surface; and coupling the cushion to a rail of the operating table such that the attendant support surface of the cushion is oriented at least partially laterally outward from the rail, the attendant support surface being operable to provide support to an attendant positioned adjacent to and leaning against the operating table.

Coupling the cushion to the rail can include attaching the cushion directly to the rail such that an interface between the cushion and the rail is devoid of any additional support structure. The operating table can include a patient support surface thereon that defines a lower vertical boundary of a sterile field, and coupling the cushion to the rail can include coupling the cushion vertically removed from the sterile field.

The cushion can include one or more weakened zones that define cushion segments, and the method can further include separating at least two cushion segments from one another at the weakened zones.

The method can further include slidably positioning the cushion along the rail. Attaching the cushion to the rail can further include removably attaching the cushion to the rail. The cushion can include a rail opening on a side of the cushion opposite the attendant support surface, and coupling the cushion to the rail can include elastically deforming walls of the rail opening and installing the cushion about the rail.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

I claim:

1. An operating table assembly, comprising:
   a base;
   a patient support surface carried by the base, the patient support surface configured to receive and support a patient thereon;
   a rail carried by the base, the rail extending along a lateral side of the operating table, the rail being disposed vertically lower than the patient support surface and presenting an inner surface, proximal to the base and an outer surface, distal from the base; and
   a cushion, coupled to the rail, the cushion having an inner surface proximal to and contacting the outer surface of the rail and an outer surface located distally from the outer surface of the rail, the outer surface of the cushion presenting an attendant support surface disposed vertically lower than the patient support surface and oriented at least partially laterally outward from the rail, the attendant support surface operable to provide support to an attendant positioned adjacent to and leaning against the operating table.

2. The assembly of claim 1, wherein the cushion is coupled directly to the rail such that an interface between the cushion and the rail is devoid of any additional support structure.

3. The assembly of claim 1, wherein the patient support surface defines a lower vertical boundary of a sterile field, and wherein the rail and the cushion are vertically removed from the sterile field.

4. The assembly of claim 1, wherein the cushion presents an at least partially arcuate attendant support surface.

5. The assembly of claim 1, wherein the cushion includes one or more weakened zones that define cushion segments, the cushion segments being separable from one another at the weakened zones.

6. The assembly of claim 1, wherein the cushion is slidably positionable along the rail.

7. The assembly of claim 1, wherein the cushion is removably attachable to the rail.

8. The assembly of claim 1, wherein the cushion is at least partially deformable to provide a form fit over the rail.

9. The assembly of claim 8, wherein the cushion includes a rail opening on a side of the cushion opposite the attendant support surface, the rail opening being openable to receive at least a portion of the rail within the cushion.

10. A method of providing an attendant support on an operating table, the operating table including a base, and a patient support surface and a rail carried by the base, the rail extending along a lateral side of the operating table vertically lower than the patient support surface, the method comprising:
    obtaining a cushion having an inner surface and an outer surface, the outer surface presenting an attendant support surface;
    coupling the cushion to the rail of the operating table such that an inner surface of the cushion is proximal to and contacts an outer surface of the rail and the attendant support surface of the cushion is disposed vertically lower than the patient support surface and distal to the outer surface of the rail and is oriented at least partially laterally outward from the rail, the attendant support surface being operable to provide support to an attendant positioned adjacent to and leaning against the operating table.

11. The method of claim 10, wherein coupling the cushion to the rail comprises attaching the cushion directly to the rail such that an interface between the cushion and the rail is devoid of any additional support structure.

12. The method of claim 10, wherein the operating table includes a patient support surface thereon that defines a lower vertical boundary of a sterile field, and wherein coupling the cushion to the rail includes coupling the cushion vertically removed from the sterile field.

13. The method of claim 10, wherein the cushion includes one or more weakened zones that define cushion segments, and further comprising separating at least two cushion segments from one another at the weakened zones.

14. The method of claim 10, wherein coupling the cushion to the rail includes slidably coupling the cushion to the rail and further comprising slidably positioning the cushion along the rail.

15. The method of claim 10, wherein attaching the cushion to the rail further comprises removably attaching the cushion to the rail.

16. The method of claim 10, wherein the cushion includes a rail opening on a side of the cushion opposite the attendant support surface, and wherein coupling the cushion to the rail includes elastically deforming walls of the rail opening and installing the cushion about the rail.

17. A kit, comprising:
a cushion, coupleable to a rail of an operating table, the cushion presenting an attendant support surface orientable at least partially laterally outward from the rail when the cushion is coupled to the rail, the attendant support surface being disposed vertically lower than the patient support surface and being operable to provide support to an attendant positioned adjacent to and leaning against the operating table, the cushion including a rail opening on a side of the cushion opposite the attendant support surface, the rail opening of the cushion being openable to receive at least a portion of the rail within the cushion; and
instructions for attaching the cushion to the rail such that the attendant support surface is oriented laterally away from the operating table to allow the attendant to lean against the operating table when positioned laterally adjacent to the operating table.

18. The kit of claim 17, wherein the operating table includes a patient support surfaces that defines a lower vertical boundary of a sterile field, and wherein the instructions include further instructions to attach the cushion to the rail in a location vertically removed from the sterile field.

19. The kit of claim 17, wherein the cushion includes one or more weakened zones that define cushion segments, and wherein the instructions include further instructions to separate cushion segments one from another at the weakened zones.

20. The kit of claim 17, wherein the cushion is slidably positionable along the rail, and wherein the instructions include further instructions to slidably position the cushion along the rail.

\* \* \* \* \*